United States Patent [19]

Antranikian et al.

[11] Patent Number: 5,346,821
[45] Date of Patent: Sep. 13, 1994

[54] THERMOSTABLE PROTEASE FROM STAPHYLOTHERMUS

[75] Inventors: Garabed Antranikian, Seevetal 1-Hittfeld; Michael Klingeberg, Gronau, both of Fed. Rep. of Germany

[73] Assignee: Novo Nordisk A/S, Bagsvaerd, Denmark

[21] Appl. No.: 949,491

[22] PCT Filed: Jun. 14, 1991

[86] PCT No.: PCT/DK91/00159
§ 371 Date: Oct. 22, 1992
§ 102(e) Date: Oct. 22, 1992

[87] PCT Pub. No.: WO90/15621
PCT Pub. Date: Dec. 27, 1990

[30] Foreign Application Priority Data

Jun. 15, 1990 [DK] Denmark .................. 1460/90

[51] Int. Cl.$^5$ .................. C12N 9/50; C12N 9/52; C12N 9/48; C11D 10/00
[52] U.S. Cl. .................. 435/220; 435/212; 435/219; 252/174.12
[58] Field of Search .................. 435/212, 219; 252/220, 252/174.12

[56] References Cited

U.S. PATENT DOCUMENTS 3,796,635  3/1974  Delente .................. 195/65
4,480,036 10/1984  Morgan et al. .................. 435/220

FOREIGN PATENT DOCUMENTS

WO90/10072  9/1990  PCT Int'l Appl. .

OTHER PUBLICATIONS

Cowan et al. (1987) *Biochem. J.*, 247, 121–133.
Kelly et al. (1988) *Biotechnol. Prog.*, 4(2), 47–62.
Fiala et al. (1986) *System, Appl. Microbiol.*, 8, 106–113.
Cowan et al. (1985) *Trends Biotechnol.*, 3(3), 68–72.
Bragger et al. (1989) *Appl. Microbiol. Biotechnol*, 31(56) 556–561.
Cowan et al. (1982) *Biochem, Biophys Acta*, 705, 293–305.
Stetter et al. (1986) *Experientia*, 42(11/12), 1187–1191.
Fusek et al. (1990) *J. Biol. Chem.*, 265(3), 1496–1501.
Daniel (1992) *Origin Life & Evol. in Biosphere*, 22, 33–42.
Eggen et al. (1990) *FEMs Microbiol. Lett.*, 71(½), 17–20.
Klingeberg et al. (1991) *Appl. Microbiol. Biotechnol.*, 34(6), 715–719.
Blumenthals et al. (1990) *Appl. Environ. Microbiol.*, 56(7), 1992–1998.
Borman (4 Nov. 1991) *Chem. Eng. News*, 31–34.
Zamost et al., Chem. Abs. No. 117332y, vol. 114, No. 13, p. 308 (1990).
Takii et al., Chem. Abs. No. 127292a, vol. 108, No. 15, p. 332 (1987).
Meito Sangyo Co., Ltd., Chem. Abs. No. 2625z, vol. 82, No. 1, p. 244 (1974).
Inoue et al., Chem. Abs. No. 6098r, vol. 112, No. 1, p. 618 (1990).
Tosh Corp., Patent Abs. of JP No. C551, vol. 12, No. 472 (1988).

*Primary Examiner*—David M. Naff
*Assistant Examiner*—Jon P. Weber
*Attorney, Agent, or Firm*—Steve T. Zelson; Elias J. Lambiris

[57] ABSTRACT

This invention is within the field of thermostable proteases. More specifically, the present invention relates to a thermosetable protease from Staphylothermus marinus, a process for the preparation of these enzymes, and detergent compositions comprising these enzymes. The enzyme has a temperature optimum in the range of from 90°–100° C. and a pH optimum in the range of from 6.5–10.

14 Claims, 1 Drawing Sheet

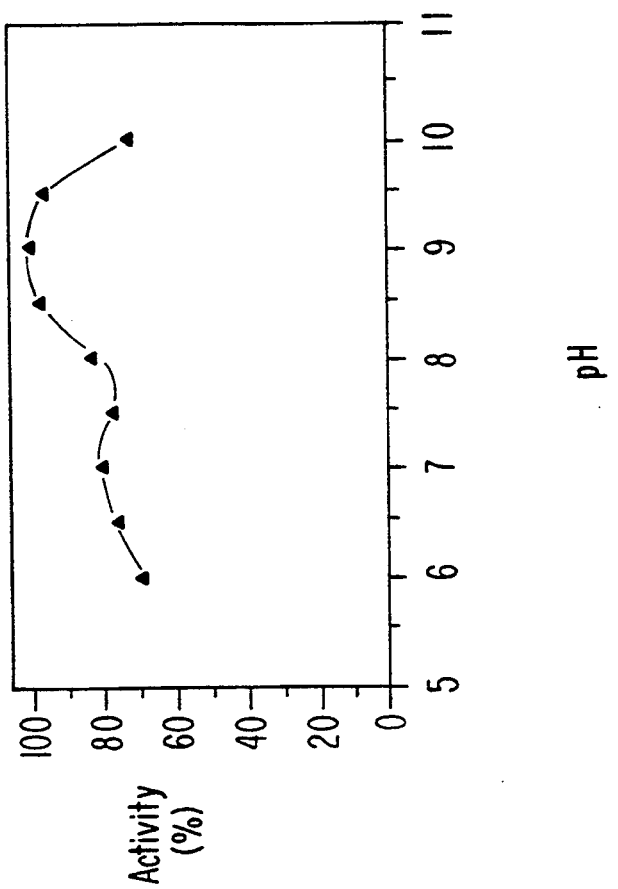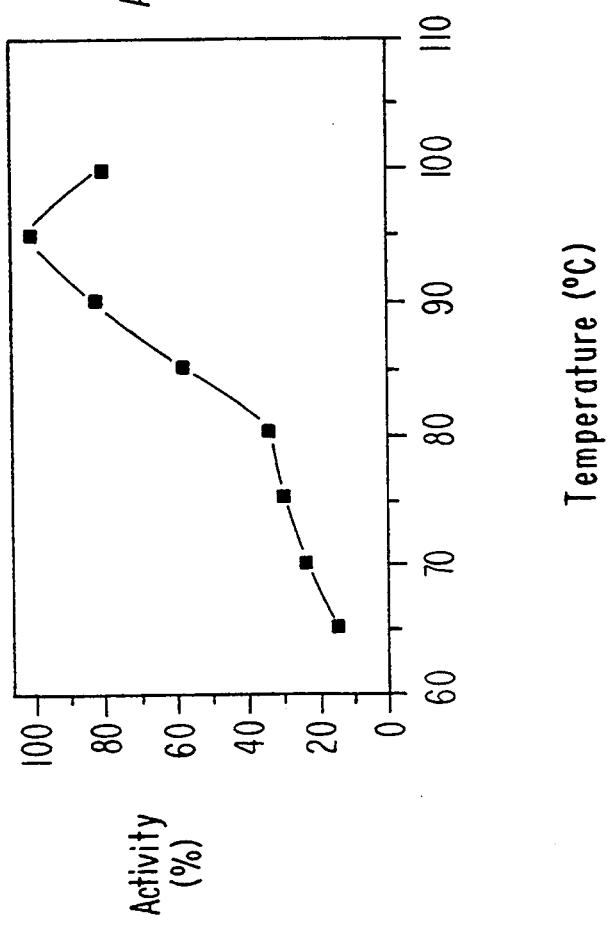
FIG. 1A
FIG. 1B

THERMOSTABLE PROTEASE FROM STAPHYLOTHERMUS

TECHNICAL FIELD

This invention is within the field of thermostable proteases. More specifically, the present invention relates to novel thermostable proteases, to a process for the preparation of these enzymes, and to detergent compositions comprising these enzymes.

BACKGROUND ART

Hyperthermophilic archaebacteria have been isolated from solfataric and submarine hydrothermal systems (Kelly, R. M. & Deming, J. W.; Biotech. Progress, 4, 47–62 (1988)). It has been presumed that members of Pyrococcus and Thermococcus contain heat stable proteases and amylases (Stetter, K. O.; J. Chem. Technol. Biotechnol., 43(4), 315–317 (1988)), but proteases obtainable from members of Staphylothermus have never been predicted, isolated or in other ways investigated.

BRIEF DISCLOSURE OF THE INVENTION

Within the scope of the present invention novel enzymes that show extraordinary thermostability as well as thermoactivity are provided. Accordingly, in its first aspect, the present invention provides a protease that is characterized by having pH optimum in the range of from pH 6.5 to 10, and temperature optimum in the range of from 90° to 100° C. In another aspect, the present invention provides a protease that is characterized by having pH optimum in the range of from pH 6.5 to 10, temperature optimum in the range 90° to 100° C., and immunochemical properties identical or partially identical to those of the protease derived from *Staphylothermus marinus*, DSM No. 3639.

In a third aspect, the present invention provides a process for the preparation of the thermostable proteases of the invention, which process comprises cultivation of a protease producing strain of staphylothermus in a suitable nutrient medium, containing carbon and nitrogen sources and inorganic salts, followed by recovery of the desired enzyme. In preferred embodiments of this process, a strain of *Staphylothermus marinus*, preferably *Staphylothermus marinus*, DSM No. 3639, or a mutant or a variant thereof, is cultivated.

BRIEF DESCRIPTION OF THE DRAWING

The present invention is further illustrated by reference to the accompanying drawing, in which FIGS. 1A and 1B show the relation between the proteolytic activity of the protease obtained from *Staphylothermus marinus*, and temperature and pH, respectively.

DETAILED DISCLOSURE OF THE INVENTION

Growth experiments with Staphylothermus have now shown that these organisms secrete extremely thermostable and thermoactive protein hydrolyzing enzymes. These enzymes possess proteolytic activity under extreme conditions. The properties of the Staphylothermus proteases are demonstrated by the protease obtained from *Staphylothermus marinus*. A strain of *Staphylothermus marinus* is available from DSM, No. 3639.

As appears from the Figure, the protease obtainable from *Staphylothermus marinus* is active in a broad temperature and pH range, namely at temperatures of from below 65° C. to above 100° C., and at pH values of from below pH 6 to above 10. The temperature optimum is between 90° and 100° C., around 95° C. Approximately 80% of proteolytic activity is still detected at 100° C. Moreover, it appears from the Figure that the relation between protease activity and pH leads to a flat activity curve, which means that the protease is very pH tolerant, possessing a generally high proteolytic activity over a broad pH range. In this way the proteases according to the invention have pH optimum in the range of from pH 6.5 to 10, more specifically between pH 8 and pH 10, yet more specifically between pH 8.5 and pH 9.5, around pH 9. At pH 6 and 10, respectively, approximately 70% of proteolytic activity is detected.

In table 1 some of the properties of the proteases obtainable from Staphylothermus sp. are shown.

TABLE 1

|  | *Staphylothermus marinus* |
|---|---|
| pH optimum | 9.0 |
| temperature optimum | 95° C. |
| type | serine |
| substrate specificity: |  |
| Z-DL-Arg-pNA | − |
| Suc-Ala-Ala-Pro-Phe-pNA | + |
| Z-DL-Lys-pNA | + |
| Z-Gly-Pro-pNA | − |
| D-Phe-Pip-Arg-pNA | − |
| D-Val-L-Leu-Lys-pNA | + |

Suc = succinyl
pNA = p-nitroanilide
Pip = piperazine

IMMUNOCHEMICAL PROPERTIES

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Preparation of the Proteases

The proteases according to the present invention are obtainable from members of the genus Staphylothermus, e.g. *Staphylothermus marinus*.

The proteases of the invention can be prepared by cultivation of a protease producing strain of members of Staphylothermus in a suitable nutrient medium, containing carbon and nitrogen sources and inorganic salts, and thus harvesting the desired enzyme.

The protease according to the present invention can also be prepared by recombinant DNA-technology.

Detergent Compositions

Due to the unique properties of the proteases according to the present invention, these enzymes are of great interest for industrial applications, e.g. for use in the detergent industry.

The detergent composition of the invention may comprise one or more surfactants, which may be of an anionic, non-ionic, cat-ionic, amphoteric or zwitterionic type, or a mixture of these. Typical examples of anionic surfactants are linear alkyl benzene sulfonates (LAS); alkyl sulfates (AS); alpha olefin sulfonates (AOS); alcohol ethoxy sulfates (AES) and alkali metal salts of natural fatty acids. Examples of nonionic surfactants are alkyl polyethylene glycol ethers; nonylphenol polyethylene glycol ethers; fatty acids esters of sucrose and glucose; and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases; amylases; cellulases; and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced according to e.g. GB 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol; a sugar or sugar alcohol; lactic acid or boric acid, according to established methods. Other enzyme stabilizers are wellknown in the art. Protected enzymes may be prepared according to the method disclosed in EP 238,216.

The following examples further illustrate the present invention.

EXAMPLE 1

Cultivation of Staphylothermus marinus

Staphylothermus marinus, DSM No. 3639, was cultivated in a nutrient medium containing the following components (per liter):

| Seasalt | 30 g |
|---|---|
| $KH_2PO_4$ | 1.5 g |
| $NiCl_2.6H_2O$ | 2 mg |
| Trace element solution (see DSM medium 141) | 10 ml |
| Yeast extract | 1 g |
| Peptone | 5 g |
| Resazurine | 1 mg |
| Sulphur powdered | 10 g |
| $Na_2S.9H_2O$ | 0.5 g |

-continued

| | |
|---|---|
| pH 6.3–6.5, 88° C. | |

The medium without sodium sulphide and sulphur was boiled for 20 minutes, cooled on ice and dispensed under $N_2$ atmosphere. The medium was then filled under $N_2$ atmosphere into 100-ml vials containing sulphur. For sterilization the medium was heated to 100° C. for 1 hour on each of 3 successive days.

Before inoculation the medium was reduced by adding 10 ml/l of sterile neutral sodium sulphide (5% solution). The medium was inoculated with 10% of a grown preculture and finally incubated at 88° C. for 48–58 hours.

Assay for Proteolytic Activity

The assay mixture contained 0.25% casein (Hammarsten) which was dissolved in 50 mM Tris/Glycine buffer, pH 9.0. The reaction was initiated by the addition of 250 μl enzyme sample to 2250 μl assay mixture at 90° C. Samples (500 μl each) were taken after 30, 60, 90 and 120 min. The reaction was stopped by cooling on ice and after the addition of trichloroacetic acid (10% solution). The mixture was allowed to stand at room temperature for about 30 minutes and centrifugated afterwards for 10 minutes at 12,000 r.p.m. The absorbance of the supernatant was determined at 280 nm against a blank. 1 U of enzyme is defined as that amount of enzyme which liberates 1 μmol of tyrosine per minute under the specified conditions.

Characterization of the Protease

Casein (Hammerstein) was dissolved at a concentration of 0.25% in a buffer mixture which was composed of 20 mM MES (2-[N-Morpholino]ethanesulfonic acid), 20 mM HEPES (N-2-hydroxyethylpiperazine-N'-2-ethanesulfonic acid) and 20 mM Glycine at pH-values of from 6 to 10, and at temperatures of from 65° to 100° C.

As shown in the Figure, the level of protease activity reached a maximum between pH 8 and 10, around pH 9. At a pH value of 6 and 10, respectively, approximately 70% of proteolytical activity could be detected. Optimum proteolytic activity for the substrate casein occurred at 95° C. Approximately 80% of enzyme activity was measured at 100° C., and approximately 20% of enzyme activity was measured at 65° C.

We claim:

1. An isolated protease having the following properties:
   (a) a pH optimum in the range of 6.5 to 10.0;
   (b) a temperature optimum in the range of 90° to 100° C.; and
   (c) immunochemical properties identical to those of the protease obtained from the strain *Staphylothermus marinus*, DSM No. 3639.

2. The isolated protease according to claim 1 which is obtained from a strain of Staphylothermus.

3. The isolated protease according to claim 2 which is obtained from a strain of *Staphylothermus marinus*.

4. The isolated protease according to claim 3 which is obtained from the strain *Staphylothermus marinus*, DSM No. 3639.

5. An isolated protease according to claim 1 which has a pH optimum in the range of 8.0 to 10.0

6. An isolated protease according to claim 5 which has a pH optimum in the range of 8.5 to 9.5.

7. An isolated protease according to claim 6 which has a pH optimum of around 9.0.

8. An isolated protease according to claim 1 which has a temperature optimum of around 95° C.

9. A process for the preparation of the protease according to claim 1, comprising cultivating a protease producing strain of Staphylothermus in a suitable nutrient medium containing carbon and nitrogen sources and inorganic salts and recovering the protease.

10. The process according to claim 9, wherein the protease producing strain is a strain of *Staphylothermus marinus*.

11. The process according to claim 9, wherein the protease producing strain is *Staphylothermus marinus*, DSM 3639.

12. A proteolytic detergent additive, comprising an isolated protease according to claim 1 in combination with a suitable excipient, said detergent additive being provided in the form selected from the group consisting of a non-dusting granulate, a liquid or a stabilized liquid, a slurry, and a protected enzyme.

13. A detergent composition comprising an isolated protease according to claim 1 and a surfactant.

14. The detergent composition according to claim 13, further comprising one or more other enzymes selected from the group consisting of an amylase, a lipase, a cellulase, and a peroxidase.

* * * * *